(12) United States Patent
Meyer et al.

(10) Patent No.: US 6,696,490 B2
(45) Date of Patent: Feb. 24, 2004

(54) SLOW RELEASE INSECT REPELLENT COMPOUNDS AND PROCESS FOR DELIVERING ACTIVE

(75) Inventors: Frank Meyer, Fort Lee, NJ (US); Ferial Khorshahi-Arvanaghi, Franklin Lakes, NJ (US); Bijan Harichian, Warren, NJ (US); Victor DeFlorio, Cranford, NJ (US); Yu-Wen Feng, Cliffside Park, NJ (US)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 22 days.

(21) Appl. No.: 10/192,468

(22) Filed: Jul. 10, 2002

(65) Prior Publication Data

US 2004/0014811 A1 Jan. 22, 2004

(51) Int. Cl.[7] .................. A01N 37/02; A01N 37/06; A01N 37/36
(52) U.S. Cl. .............. 514/546; 514/547; 514/548; 514/549; 514/552; 514/919
(58) Field of Search .................. 514/546, 547, 514/548, 549, 552, 919

(56) References Cited

U.S. PATENT DOCUMENTS

| 4,774,082 A | 9/1988 | Flashinski et al. ... 424/DIG. 10 |
| 5,621,013 A | 4/1997 | Beldock et al. ............. 514/703 |
| 6,015,570 A | 1/2000 | Tucci et al. ................. 424/403 |
| 6,180,127 B1 | 1/2001 | Calton et al. ............... 424/409 |

FOREIGN PATENT DOCUMENTS

| EP | 0 348 550 B1 | 5/1993 |
| EP | 0 502 119 B1 | 1/1996 |
| JP | 3-56442 | * 3/1991 |

OTHER PUBLICATIONS

File JPAB an WEST, publication No. JP403056442A, abstracting JP 3–56442 (1991).*

* cited by examiner

*Primary Examiner*—John Pak
(74) *Attorney, Agent, or Firm*—Ronald A. Koatz (57) ABSTRACT

Novel insect repellents having ester bonds such that when deposited on skin, natural skin cleaning agents provide slow release of the active.

2 Claims, 7 Drawing Sheets

Figure 1

Figure 2: Schematic drawing of Solid-Phase-Microextraction (SPME) experiment

Figure 3a – Solid Phase Micro Extraction (SPME) followed by GC-MS analysis of PMDL (Monitoring PMD released form hydrolysis of PMDL on the skin)*

*PMD is the hydrolysis product of the originally applied PMD-L.

Figure 3b. Solid Phase Micro- Extraction (SPME) followed by GC-MS analysis of PMD released from skin Figure 4 – Plot of chromatographic peak areas of PMD in the five skin's extract samples from GC-MS Figure 5 – Concentration of PMDL in five skin's extract samples from GC-MS over time Figure 6 - Plot of chromatographic peak areas and its standard deviations for linoleic acid in the five skin extract samples from full mass scan experiment.

SLOW RELEASE INSECT REPELLENT COMPOUNDS AND PROCESS FOR DELIVERING ACTIVE

FIELD OF THE INVENTION

The invention relates to novel insect repellents (e.g., 3,8-p-Menthanedilinoleate, also known as PMDL) having ester bonds such that, when deposited on skin, natural cleaving agents in the skin cleave the ester bonds and provide slow release of the repellent active. The invention further relates to a process for slowly delivering (e.g., over time) the insect repellent active to skin or other substrate by providing novel compounds, which are esters of known actives, to the skin or substrate surface thereby allowing skin esterases to cleave ester bonds and release the active.

BACKGROUND OF THE INVENTION

One of the major technical problems in the area of insect repellent applied to skin is that the skin repellent active (e.g., N,N diethyl diamide, also known as DEET; or para-menthane-3,8, diol, also known as PMD) evaporates too quickly such that the life span of the active is shorter than optimally desirable (e.g., 1 to 2 hours rather than longer, slow release). Thus, it requires constant reapplication.

Methods for controlled release of repellent molecules are known in the art.

EP 348 550 (assigned to Showa Denko), for example, discloses use of microcapsules (filled with diethyltoluamide active) to provide slow release of active. These are referred to as vermin-repellent microcapsules.

EP 502 119 (assigned to Scios Nova) discloses use of solid, water-insoluble liposphere (formed of a solid hydrophobic core having a layer of a phospholipid embedded on the surface of the core) for extended release of active (e.g., insect control agent).

U.S. Pat. No. 6,015,570 to Tucci et al. discloses a slow release insect repellent, an oleophillic chemical soluble in the insect repellent and a matrix wherein the combination of insect repellent and oleophillic chemical are entrapped in said matrix and slowly released from a substrate (e.g. fabric substrate) containing them.

U.S. Pat. No. 4,774,082 to Flashinski et al. discloses compositions in which polymer is used to decrease volatility of insect repellent and clearly enhance residual activity.

Similarly, U.S. Pat. No. 6,180,127 to Calton et al. disclose use of copolymer of polyvinyl pyrollidone and an alkyl group of 4–30 carbon for slow release of volatile repellent.

In none of these references is there disclosed esters (e.g., saturated or unsaturated, $C_8$ to $C_{30}$, preferably $C_{12}$ to $C_{24}$ fatty acid esters) of specific repellents (e.g., ester of 3,8-p-menthanediol) as novel compounds which can be applied to skin (e.g., solubilized in alcohol solution and applied as alcohol based solution), wherein natural enzymes in the skin (e.g., esterases) are permitted to provide slow release of the repellent active. Use of these esters permits the dual function of delivery of repellent active (cleaved from fatty acid portion) as well as delivery of skin benefit agent (e.g., fatty acid benefit agent such as linoleic acid).

Finally, the underlying actives are not new. Thus, for example 3,8, para-methanediol (known also as "Chinese Crystal"), used as an example in the subject invention, is a known insect repellent as disclosed in U.S. Pat. No. 5,621,013. Again, however, the use of novel esters of such actives (e.g., 3,8-p-methane linoleate, or PMD-L) as slow release insect repellent is not, to applicants' knowledge, known.

BRIEF DESCRIPTION OF THE INVENTION

Suddenly and unexpectedly, applicants have found that esters of insect repellents, e.g., saturated or unsaturated $C_8$ to $C_{30}$, preferably $C_{12}$–$C_{24}$ esters of such repellents serve as slow release compounds, especially when formulated and delivered to skin or other substrates.

In a second embodiment of the invention the invention relates to compositions, which may, but need not, contain surfactant and which compositions may be delivered as leave on or wash off compositions to the skin surface. These compositions, of course, comprise the ester derivatives of insect repellent such as those noted above.

Finally, the invention provides a method for providing insect repellent compound over a period of greater than about 3 hours, as measured by Solid Phase Micro Extraction/gas chromatography of head space above skin or substrate which has been treated with the repellent compound (i.e., repellent active precursor such as, for example, PMD-L).

BRIEF DESCRIPTION OF THE DRAWINGS

FIG. 3b also tracks concentration of PMD measured by SPME. In this graph, for calibration purposes, the PMD was applied neat to the skin rather than having been hydrolyzed from PMD-L.

FIG. 4 shows decrease of PMD attributable to a evaporation of PMD from skin to surrounding environment.

As can be seen, PMD-L was applied to the skin and the mass of free linoleic acid was detected. As time proceeded, the decay of PMD-L increases producing more free linoleic acid as compared to the blank and the starting values.

DETAILED DESCRIPTION OF THE INVENTION

The present invention relates to novel ester compounds comprising skin repellent benefit agent which benefit agent can be delivered to the skin in wash off or leave on products. These esters slowly release benefit agent repellent (i.e., PMD) to the skin upon hydrolysis of the ester. In a second embodiment, the invention relates to compositions containing said ester compounds and to a process of delivering to the skin said esters comprising skin repellent active. The process permits that repellent active be delivered for greater than 3 hours as measured by SPME/gas chromatography of head space above skin or substrate. As indicated in the figures (see FIG. 4), when delivered in non-ester form, active (i.e., PMD) is no longer present after 2.5 hours.

In a first embodiment, the invention relates to a fatty acid ester of a known insect repellent.

The fatty acid ester is a $C_8$ to $C_{30}$, preferably $C_{12}$ to $C_{24}$ saturated or unsaturated fatty acid ester of skin repellent active.

The repellent active (i.e., PMD) of the invention should have at least one hydroxyl group accessible to a carboxylate group of a fatty acid such that an ester bond can be formed. The fatty acid chain of the acid should be a saturated or unsaturated $C_8$ to $C_{30}$ chain.

A preferred example of a repellent with an accessible hydroxyl group is 3,8-p-menthanediol or PMD.

Examples of fatty acid which may link to the hydroxyl and form the novel cleavable esters of the invention include saturated acids such as stearic acid or behenic acids, or unsaturated acids such as linoleic.

An example of how the ester is formed from PMD and fatty acid is shown as follows:

(I)

Thus, for example, when the acid halide in equation I above is linoleyl chloride, the benefit agent comprising repellent is PMD-linoleate. As noted, this too can then subsequently be hydrolyzed in skin to form PMD and linoleic acid.

In a second embodiment, the invention relates to personal wash and/or personal care compositions comprising the repellent esters of the invention.

The compositions may be delivered, for example, in the form of liquid cleansers and body washes, bars, and nonwovens.

The cleanser composition, for example, may be in the form of a liquid cleanser or body wash. Generally, although not necessarily, such liquid cleansing compositions will comprise at least one surfactant. Typically, the compositions comprises 1% to 99% by wt., preferably 2% to 85%, more preferably 3% to 50% by wt. of a mild surfactant system. Since applicants have discovered a correlation between mildness and lightening, it is an important aspect of the invention that zein solubilization of the composition, whether a single surfactant, a combination of surfactants in a surfactant system or no surfactant at all are used, be less than the zein solubilization of a second composition to which it is compared. Preferably, zein solubilization of compositions of the invention should be about 2% or less, as measured by tests noted below.

If a surfactant is used, a number of anionic, nonionic, cationic, zwitterionic and/or amphoteric surfactants may be used, alone or in combination, as long as, as noted, the compositions maintain an overall zein solubility less than that of the composition against which they are compared, preferably about 2 and below.

Among suitable anionic actives which may be used are the alkyl ether sulfates, acyl isethionates, alkyl ether sulfonates, sarcosinates, sulfosuccinates, taurates and combinations thereof. Among suitable amphoteric actives may be included alkylbetaines, amidopropyl betaines, amidopropyl sultaines and combinations thereof.

Alkyl ether sulfates of the present invention will be of the general formula wherein R ranges from $C_8$–$C_{20}$ alkyl, preferably $C_{12}$–$C_{15}$ alkyl, n is an integer from 1 to 40, preferably from 2 to 9, optimally about 3, and $M^+$ is a sodium, potassium, ammonium or triethanolammonium cation.

Typical commercial co-actives of this variety are listed in the Table below:

| Trademark | Chemical Name | Physical Form | Manufacturer |
|---|---|---|---|
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycloryl TD | TEA Laureth Sulfate | Paste | Cyclo |
| Standopol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium $C_{12}$–$C_{15}$ Pareth-15 sulfonate.

Another active type suitable for use in the present invention is that of the sulfosuccinates. This category is best represented by the monoalkyl sulfosuccinates having the formula $R_2OCCH_2CH(SO_3-Na^+)COO-M^+$; and amido-MEA sulfosuccinates of the formula: $RCONHCH_2CH_2O_2CCH_2CH(SO_3-M^+)COO-M^+$; wherein R ranges from $C_8$–$C_{20}$ alkyl, preferably $C_{12}$–$C_{15}$ alkyl and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Emcol 4400-1 | Disodium Lauryl Sulfosuccinate | Solid | Witco |
| Witco C5690 | Disodium Cocoamido MEA Sulfosuccinate | Liquid | Witco |
| McIntyre | Disodium Cocoamido | Liquid | McIntyre |

-continued

| Trademark | Chemical Name | Physical Form | Manufacturer |
|---|---|---|---|
| Mackanate CM40F | MEA Sulfosuccinate | | |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula $RCON(CH_3)CH_2CO_2—M^+$, wherein R ranges from $C_8–C_{20}$ alkyl, preferably $C_{12}–C_{15}$ alkyl and $M^+$ is a sodium, potassium ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W. R. Grace |
| Hamposyl TOC-30 | TEA Cocoyl/ Sarcosinate | Liquid | W. R. Grace |

Taurates may also be employed in the present invention as co-actives. These materials are generally identified by the formula $RCONR'CH_2CH_2SO_3—M^+$, wherein R ranges from $C_8–C_{20}$ alkyl, preferably $C_{12}–C_{15}$ alkyl, R' ranges from $C_1–C_4$ alkyl, and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2—M^+$, amidopropyl betaines of the formula $RCONHCH_2CH_2CH_2N^+(CH_3)_2CH_2CO2—M^+$, and amidopropyl sultaines of the formula $RCONHCH_2CH_2N^+(CH_3)_2CH_2SO_3—M^+$ wherein R ranges from $C_8–C_{20}$ alkyl, preferably $C_{12}–C_{15}$ alkyl, and $M^+$ is a sodium, potassium, ammonium or triethanolammonium cation. Typical commercial products representative of these co-actives are found in the Table below:

| Trademark | Chemical Name | Physical Form | Manufacturer |
|---|---|---|---|
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula in which R denotes a linear or branched alkyl group and M denotes an alkali metal or alkaline earth metal or an amine.

Another surfactant which may be used are the monoalkyl or dialkylphosphate surfactants.

Another mild surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA-, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high foaming is desirable; however, they can be incorporated as a co-surfactant.

Nonionic and cationic surfactants which may be used include any one of those described in U.S. Pat. No. 3,761,418 to Parran, Jr., hereby incorporated by reference into the subject application. Also included are the aldobionamides as taught in U.S. Pat. No. 5,389,279 to Au et al; and the polyhydroxy fatty acid amides as taught in U.S. Pat. No. 5,312,934 to Letton, both of which are incorporated by reference into the subject application.

Soaps may be used at levels of about 0.1 to 10%. Soaps can be used at higher level (for example, to provide soap-like feel) provided that the overall surfactant mixture is milder than soap and retains zein values within the scope of the invention. The soaps may be added neat or made in situ via adding a base, e.g., NaOH; to convert free fatty acids.

Of course, as noted above, soaps should only be used as cosurfactants to the extent that zein solubilization of composition is less (milder) than a composition to which compared, preferably about 2 and below.

A preferred surfactant active system is one such that acyl isethionate comprises 1 to 15% by weight of the total composition and/or an anionic other than acyl isethionate (e.g., ammonium lauryl ether sulfate) comprises 1 to 15% by weight of the total composition and amphoteric comprises 0.5 to 15% by weight of the total composition.

Another preferred active system is one comprising 1 to 20% alkyl ether sulfate. Preferred surfactant active systems may also contain 1 to 10% alkali metal lauryl sulfate or $C_{14}$–$C_{16}$ olefin sulfonate instead of acyl isethionate.

The cleansing products may be structured using, for example, external structurants such as cross-linked polyacrylates and/or clays or they may be structured with other components (e.g., unsaturated and/or branched long chain $C_8$ to $C_{24}$ liquid fatty acid or ester derivatives) which would cause the liquid to have a "lamellar" structure as described, for example, in U.S. Pat. No. 5,952,286.

The liquid products may have other ingredients typically found in liquid cleansers. Among these are included (without limitation) auxiliary thickeners (e.g., carboxymethyl cellulose, hydroxyethylcellulose); perfumes; sequestering agents (e.g., ethyl diamine tetra acetate, known as EDTA); coloring agents; opacifiers and pearlizers (e.g., zinc or magnesium stearate, titanium dioxide).

Other optionals include antimicrobial agents; preservatives (e.g., parabens, sorbic acid); suds boosters (e.g., coconut acyl mono- or diethanolamide); antioxidants; cationic conditioners (e.g., Merquat® and Jaguar® type conditioners); polyalkylene glycols, glycerin and other water-soluble conditioning agents; thickeners; exfoliates; ionizing salts; organic acids (e.g., citric or lactic acid).

In a preferred embodiment of the invention, the compositions may comprise on oil/emollient.

Among oils which can be used are:

Vegetable oils: Examples include orachis oil, castor oil, cocoa butter, coconut oil, corn oil, cotton seed oil, olive oil, palm kernel oil, rapeseed oil, safflower seed and sesame seed oil, soybean oil.

Ester: Examples include butyl myristate, cetyl palmitate, glyceryl stearate or isostearate, isobutyl, palmitate, isopropyl isostearate, isopropyl myristate.

Other classes of oil/emollient include animal fats (lanolin, lard), fatty acids and alcohols (behenic acid, palmitic acid, stearic acids, cetyl alcohol).

Further are included mineral oil, petrolatum, silicone oil.

The compositions of the invention may also be delivered in the form of a bar composition.

Bar compositions may comprise 5% to 90% by wt. of a surfactant wherein the surfactants may be any of the surfactants noted above (e.g., anionics, nonionics, amphoteric/zwitterionics, cationics) or mixtures thereof. As with liquid cleansers noted above, the amount of pure soap actually used is preferably not too high as to effect overall harshness of the bar (i.e., zein values of bar compositions are still within the scope of the invention).

The bar compositions also comprises 0.1 to 20% water, preferably 1 to 15% by wt. water.

The bar composition further comprises 0.1 to 80% by wt., preferably 5% to 75% by wt. of a structuring aid and/or inert filler. Such structurants can be used to enhance the bar integrity, improve the processing properties, and enhance desired user sensory profiles.

The structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200-glyceryl-stearate, glucam DOE 120 (PEG Methyl Glucose Dioleate), and Hodg CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

In addition, the bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330—Polyquaternium 39; and Jaguar® type conditioners.

Polyethylene glycols as conditioners which may be used include:

| Polyox | WSR-205 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

The composition may be delivered in the form of a topical or leave-on composition.

Generally, such topical compositions will comprise some form of lipid moisturizing agent (e.g., ceramides, pseudoceramides etc.), a cosmetically acceptable vehicle (e.g., to act as diluant, dispersant or carrier for the active and/or other skin benefit materials), and cosmetic adjuncts.

As noted, such compositions generally comprise cosmetically acceptable vehicle which helps dilute, disperse or carry active components so as to facilitate their distribution when the composition is applied to skin, hair or other substrate.

Vehicles other than water can include liquid or solid emollients, solvents, humectants, thickeners and powders.

An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable vehicle will usually form from 5 to 99.9%, preferably from 25 to 80% by weight of the composition, and can, in the absence of other cosmetic adjuncts, form the balance of the composition.

Among other skin benefit/cosmetic agents which may be used are included hydroxy acids (e.g., alpha hydroxy acids, beta hydroxy acids, other hydroxy carboxylic acids such as dihydroxy carboxylic acid); retinoids (e.g., retinoic acid, retinol, retinal and retinol esters); steroid hormones (e.g., glucocorticoids, androgens, estrogens); essential fatty acid (e.g., linoleic acid, arachidonic and others which are needed in plasma membrane formation); lipid precursors (e.g., mevalonic acid for cholesterol, phytosphingosine for ceramides) and sphasphatidic acid.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric and combinations thereof as discussed above.

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic, leave-on compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, anti-acne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Additional vitamins may also be included in the compositions of the present invention. Especially preferred is vitamin A palmitate (retinol palmitate) and vitamin E linoleate (tocopheryl linoleate). Other esters of vitamins A and E may also be utilized.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, imidazolidinyl urea, sodium dihydroxy acetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

In a third embodiment of the invention, the invention provides a process for delivering to the skin insect repellent wherein said process comprises preparing an ester of said repellent as noted above and delivering to skin in form of personal wash and/or personal care compositions.

Finally, the invention provides a method for enhancing insect repellency using the compounds and compositions noted above. Specifically, repellency can be delivered for at least greater than about 3 hours to about 24 hours, preferably 3 to 20 hours.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Materials

The starting material, 3,8-p-menthanediol (PMD) was obtained from Takasago. Reagent grade anhydrous methylene chloride, anhydrous pyridine, linoleoyl chloride and ethanol were all purchased from Aldrich Chemicals. Deuterated NMR solvents containing 99.0–99.8% deuterium in the indicated position were purchased from Cambridge Isotopic Laboratories. All chemicals were used without further purification.

Example 1

Synthesis and Identification of 3,8-p-Menthanediol Linoleate (PMDL) (Ester Which Carries Active)

Synthesis

A 250 mL one necked bottomed flask, was charged with 7.0 g (0.040 moles) of 3,8-p-menthanediol, 100 mL of anhydrous methylene chloride and 6.9 g (0.87 moles) of anhydrous pyridine. 25.5 g (0.085 moles) of Linoleoyl chloride was pre-dissolved in 25–30 mL of anhydrous methylene chloride and charged into the additional funnel. The acid chloride solution was then added dropwise to the solution at room temperature under a nitrogen blanket over a period of 30 minutes. Upon completion of the addition, the reaction was stirred for two hours before the addition funnel was replaced with a reflux condenser. The reaction was then heated to reflux for two additional hours before cooling to ambient temperature and stirring overnight.

The reaction mixture was transferred into a separatory funnel and extracted with water and with sodium bicarbonate solution. The organic layer was isolated and extracted with water before being isolated and dried. The dried organic layer was then filtered and concentrated to give 16.8 g of an amber coloured viscous liquid. The crude product was purified by silica gel chromatography.

Figure 1:
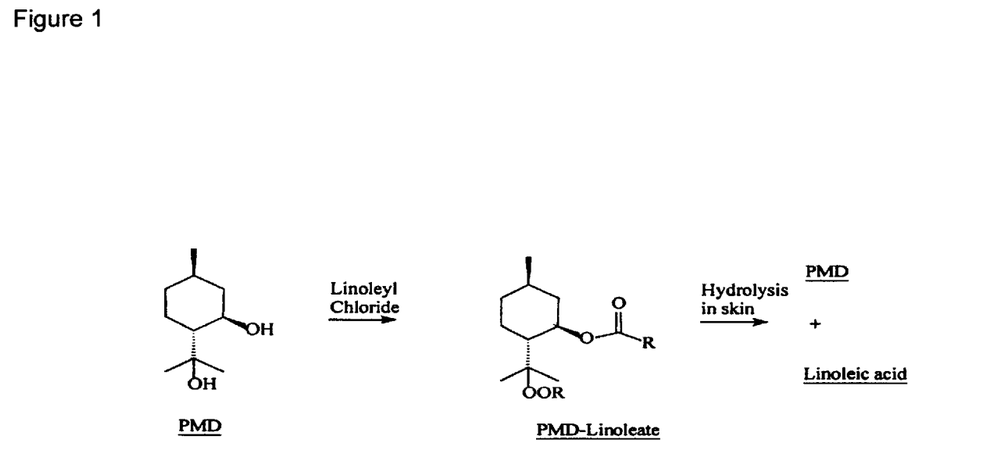
FIG. 1 is chemical depiction (schematic) of pathway from PMD to PMD-linoleate (the active to be hydrolyzed); and the subsequent hydrolysis back to PMD and linoleic acid (a by-product of hydrolysis).

The reaction of PMD (e.g., a repellent having at least one accessible hydroxy group) with linoleyl chloride (e.g., an alkali metal fatty acid) to form PMD-L is shown in FIG. 1. It is hypothesized that natural esterases found in the skin will cleave the ester bond to deliver both repellent (PMD) and free fatty acid (linoleic acid).

Identification of PMDL by NMR & IR

NMR and IR were employed to confirm the synthesis of 3,8-p-Menthanedilinoleate (PMDL) from 3,8-p-menthanediol (PMD) and Linoleic acid chloride.

Example 2

Methodology and Measurement of PMD & PMD-L

Having identified correct synthesis of PMDL, applicants sought to show that delivered levels of PMD and PMDL could be easily determined. This was done as follows:

Attenuated Total Reflection—Fourier Transform Infrared (ATR-FITR)

Instruments

FTIR was evaluated for in-vivo deposition measurements of PMD and PMDL. FTIR spectra of these repellents were acquired with a Bio-Rad FTS-60A spectrometer using a DTGS detector. A drop of oil was placed on a single-reflection zinc selenide ATR crystal and thirty-two scans at 8 $cm^{-1}$ resolution were coadded.

Experiments

Individual standard stock solutions of PMD and PMDL at concentrations of 3.26 and 3.0 $\mu g/\mu L$ were prepared by placing 0.03 g and 0.0326 g PMD and PMDL in 10 mL of absolute ethanol, respectively. A 7 cm×2 cm (14 $cm^2$) area of porcine skin samples were marked with a skin marker. FTIR spectra of the skin samples were obtained by placing the skin surface onto the ATR crystal. A clamp was used to apply constant, reproducible pressure and create even contact between the skin and crystal. In these experiments, untreated skin was first scanned to collect the spectrum of the porcine skin as reference. The skin was then dosed with 24 $\mu L$ of the respective repellent solution using a Rainin digital pipette. After each application, the skin was air-dried for five minutes before the ATR-FTIR spectrum was acquired. The procedure was repeated multiple times to build up surface coverages from 5.18 up to 84.0 $\mu g/cm^2$ of the respective repellent on the skin. Partial least squares (PLS) analysis of the spectra was used to create a calibration model. The PLSplus add-on package to GRAMS/32 v5.0 (ThermoGalactic, Salem, N.H.) was employed for this process. Spectra were mean centered and vector normalized to unit area before analysis. PLS-1 with cross validation and single file out validation was used to develop the calibration model. Parameters such as wavelength range and number of factors were adjusted until the linearity of the calibration model ($R^2$) was maximized and the standard error of cross validation [SECV] was minimized. PLS calibration results including predicted vs. actual deposition levels for both PMD and PMDL, are provided in Tables 1 and 2 below.

TABLE 1

PLS Calibration Results for PMD on Porcine Skin

| Actual Deposition ($\mu g/cm^2$) | Predicted Deposition ($\mu g/cm^2$) |
|---|---|
| 5.6 | 3.2 |
| 11.2 | 7.8 |
| 16.7 | 23.5 |
| 22.3 | 16.3 |
| 27.9 | 33.0 |
| 33.5 | 36.1 |
| 39.1 | 34.3 |
| 44.6 | 46.1 |
| 50.2 | 57.1 |
| 55.8 | 57.1 |
| 61.4 | 61.8 |
| 67.0 | 62.4 |
| 72.5 | 78.2 |
| 78.1 | 73.0 |
| 83.7 | 80.1 |

TABLE 2

PLS Calibration Results for
PMD-Lineoleate (PMD-L) on Porcine Skin

| Actual deposition ($\mu g/cm^2$) | Predicted deposition ($\mu g/cm^2$) | Residual |
| --- | --- | --- |
| 5.1 | <LOD | <LOD |
| 10.3 | 12.8 | −2.5 |
| 15.4 | 16.1 | −0.7 |
| 20.6 | 21.5 | −0.9 |
| 25.7 | 27.7 | −2.0 |
| 30.8 | 33.2 | −2.4 |
| 36.0 | 38.5 | −2.5 |
| 41.1 | 39.5 | 1.6 |
| 46.3 | 47.8 | −1.5 |
| 51.4 | 53.6 | −2.2 |
| 56.5 | 51.3 | 5.2 |
| 61.7 | 69.1 | −7.4 |
| 66.8 | 59.6 | 7.2 |
| 72.0 | 75.8 | −3.8 |
| 77.1 | 71.1 | −6.0 |
| 82.2 | 81.3 | 0.9 |

FTIR quantitative deposition model for PMD and PMDL showed that delivered levels on the skin could be easily determined. Calibration statistics for both molecules were promising.

Example 3

Tracking Measurement of PMDL (Synthesized Repellent Carrier) and of PMD and Linoleic Acid (Hydrolysis Products)

Applicants conducted a number of experiments using both solid phase micro extraction and gas chromatography in combination (SPME/GC-MS).

As discussed below, the experiments showed:

(1) that PMD repellent deposited on the skin (once slowly formed from the hydrolysis by skin of PMDL) could vaporize and release into the surrounding environment over a period of time;

(2) that although PMDL and linoleic acid cannot be detected and monitored by SPME followed by GC-MS (in the way that was PMD was detected), the hydrolysis in the skin can be monitored by following what happens to the PMD generated in skin after hydrolysis; and (3) that breakdown of PMDL into PMD and linoleic acid can be confirmed by extraction of PMDL treated skin with ethanol followed by analysis of collected extracts by GC-MS and APCI-MS. APCI-MS is defined as Atmospheric Pressure Chemical Ionization with Mass Spectrometric Detection. Specifically, the molecular ion of linoleic acid can be used to monitor this species. The results confirm the hydrolysis of PMDL by showing a decrease in the level of PMDL on the skin and a simultaneous increase in the level of PMD on the skin over an 150 minute period.

Initially the instrumentation for their analysis is discussed below.

Instrument

Solid Phase Microextraction (SPME) is a sample preparation technique which has been used for trapping volatiles. In the subject invention, SPME was used to extract and concentrate PMD vapour (by-product of PMDL hydrolysis) in the headspace. The extracted analytes were then analyzed by Gas Chromatography-Mass Spectroscopy (GC-MS). The SPME fiber used here was from Supelco, a 2.0 cm long, StableFlex fiber (23-gauge needle), 50/30 divinylenzene/carboxene on polydimethylsiloxane. Agilent 6890 Gas Chromatography equipped with Agilent 5973 Mass Selective Detector and Chemstation, G1701CA software were used for analyzing and identifying PMD. GC was equipped with a 0.25 micrometer×30 m HP-5 capillary column with 0.25 micrometer of cross-linked 5% Phenyl Methyl Siloxane. The GC oven was programmed to increase its temperature at 2 min from the initial temperature of 60° C. to 300° C. at 6° C./min. The injector temperature and the head pressure were 250° C. and 8.6 psi, respectively. The flow rate of the carrier gas (helium) was 1 mL/min The total flow rate was set at 25 mL/min Purge was off for 0.5 min, i.e. from a split mode into a splitless mode after the program was started. Agilent 5973 Mass Selective Detector with an ion source by an electron impact (EI) data system was used for mass spectrometric identification. The detector was used in a scan mode to scan mass ranging from a Low Mass of 40 to a High Mass of 550. Solvent delay time was 3.5 min. Total sample run time was 60 min.

Figure 2:
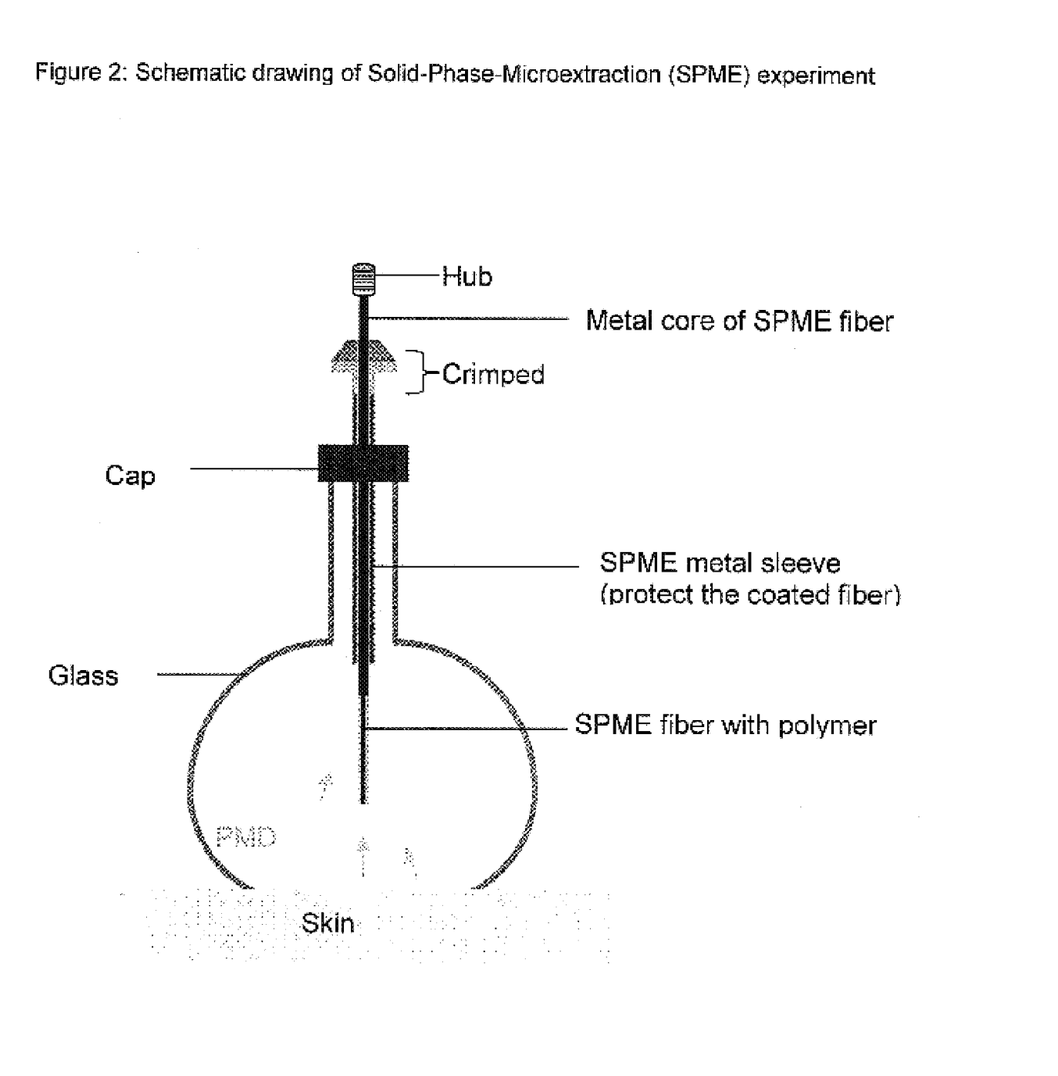
FIG. 2 is schematic of coated SPME needles used with PDMS to absorb volatile and a schematic of a device used to collect volatile from skin.

PMDL standard and ethanol skin extracts were also analyzed by GC-MS. The injection mode for PMDL was a split mode at 10:1 split ratio. The rest of conditions were the same as the ones used for PMD analysis by GC-MS as are listed above. The SPME apparently is a tube (e.g., dome or other like structure) strapped to measured area (e.g., arm) with an opening (e.g., at top) to insert analytical extractor which is essentially a needle used to trap/absorb volatiles released in the apparatus. SPME apparatus is shown in FIG. 2.

Experiments

To identify PMD by GC-MS (point (1) above), a solution of PMD in ethanol (100 $\mu g/mL$) was prepared by dissolving 1 mg PMD in 10 mL of ethanol. 1 $\mu L$ of this solution was injected into the GC-MS. To identify PMD vapour by SPME, 0.1 mg of PMD was placed in a 20 mL glass vial with an airtight cap on the top overnight to reach equilibrium between vapour and solid phases. A SPME fiber was inserted into the vial and the polymer coating on the SPME fiber was exposed to the vapour for 1 min. After absorption, the SPME fiber was transferred to GC-MS for PMD identification. Both experiments confirmed the feasibility of analysis of PMD by the above techniques. SPME coupled with GC-MS was also utilized to explore the possibility of analysis of PMDL in the same manner as described above for PMD.

To determine the extent of evaporation of PMD from the skin matrix over a period of time (correlating to amount of PMD produced by hydrolysis from PMD-L), a number of experiments were carried out. In these experiments, SPME fiber was inserted into a headspace of a glass semi-ball chamber fastened on forearm by an elastic band. The glass device had a 5 $cm^2$ opening toward the skin surface and another capped inlet for SPME insertion. A blank run (skin background) was collected prior to performing each set of experiments.

Collection and Analysis of PMD (Formed From Hydrolysis) Experiments

For a first set of SPME experiments, a PMD solution at concentration of 21800 $\mu g/mL$ was prepared by placing 0.218 g of PMD crystals in 10 mL of absolute ethanol. 80 $\mu L$ (174.4 $\mu g/cm^2$) of this solution was then placed on the marked area of the skin. The SPME glass chamber was then placed and secured on the skin as it is shown in FIG. 2. SPME fiber collected PMD vapour for a period of 30 minutes. The SPME glass chamber and fibers were then removed and the SPME fiber were analyzed by GC-MS for measurement of PMD. Forearm skin was then exposed to the air for period of 30 minute before the next sampling.

In a second experiment, the PMD levels placed on the skin and the sampling time (duration) were reduced to 40 g/cm² (14 μl of 21800 μg/mL) and 5 minute, respectively. As noted in discussion, this was to avoid flooding of GC-MS column. In order to prevent the spreading of the PMD solution beyond the marked area, the solution was placed inside a hollow glass on the surface of the skin. Then, the hollow glass was removed from the skin and replaced with the SPME glass chamber and fiber. The sampling intervals were set at 35, 70, and 105 min. The exposure time to the air between the sampling was 30 min.

In the third experiment, 40 μg/cm² of PMD was placed on the skin. The sampling intervals were set at 0, 60, 120, 180, 240 and 300 min. Extraction time by the SPME glass and fiber were increased from 5 to 30 min. The exposure time to the air in between the sampling was kept the same as previous sets and at 30 min. The GC-MS sample's run time for all the experiments was one hour.

Confirmation of Hydrolysis Based on PMD Analysis

Figure 3A:
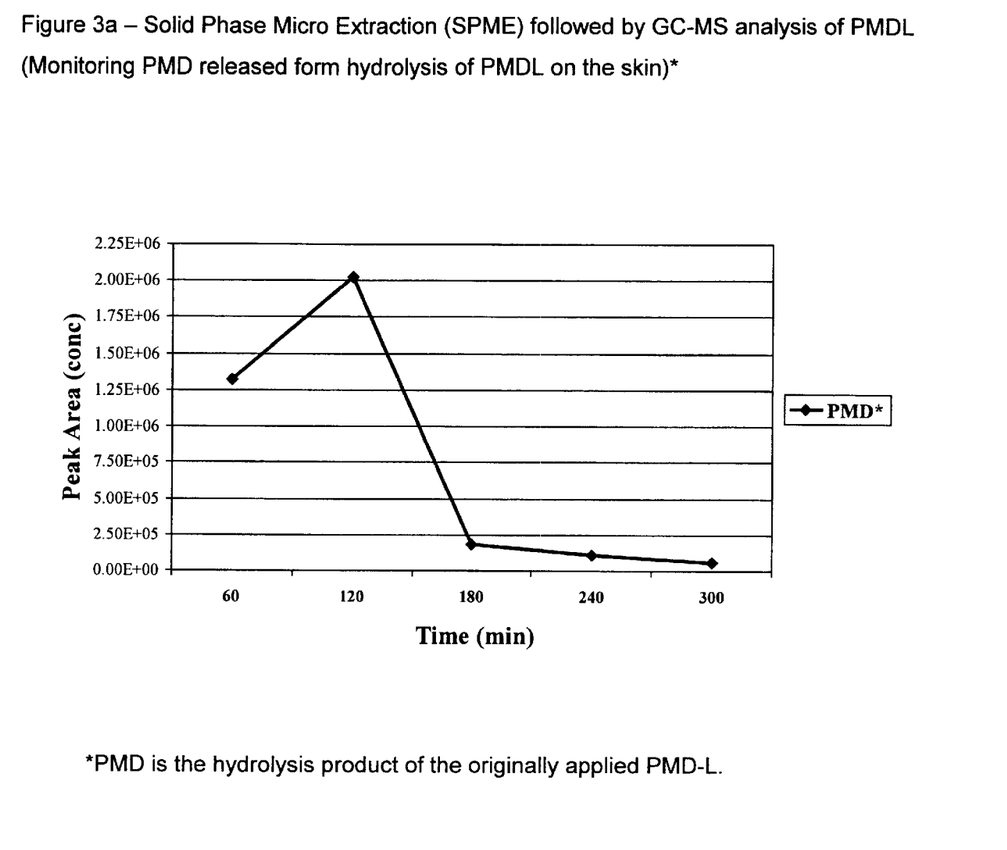
FIG. 3a is a tracking of the concentration of PMD over time as measured using solid phase micro-extraction (SPME). As seen, once PMD-L was applied to the skin, there is initial sharp increase in the concentration of PMD which decreases as the supply of PMD-L (which provides PMD upon hydrolysis) abates. This also confirms evaporation of the known repellent PMD from skin to surroundings over time.

To confirm that PMDL was being hydrolyzed into PMD and linoleic acid upon its delivery onto the skin, the following experiments were carried out. Specifically a PMDL stock solution at concentration of 19460 μg/mL was prepared by dissolving 0.0973 g PMDL oil in 5 mL of ethanol. Then, 36 μl (100 μg/cm²) of this solution was placed on the skin. SPME glass chamber and fiber were then placed on the skin for sampling. Sampling intervals were set at 0, 60, 120, 180, 240 and 300 min. The SPME chamber was removed after each sampling and the forearm skin was exposed to air. Extraction time by SPME fiber and the exposure time to air in between the sampling were 30 min each. In this set of experiments, the PMD signal generated from hydrolysis of PMDL on the skin was followed by SPME coupled with GC-MS, (see FIG. 3a). FIG. 3a clearly shows initial increase in PMD (e.g., when hydrolysis first starts) and subsequent decline (e.g., when absorbed by skin).

Analysis of PMD, PMD-L and Linoleic Acid

Figure 4:
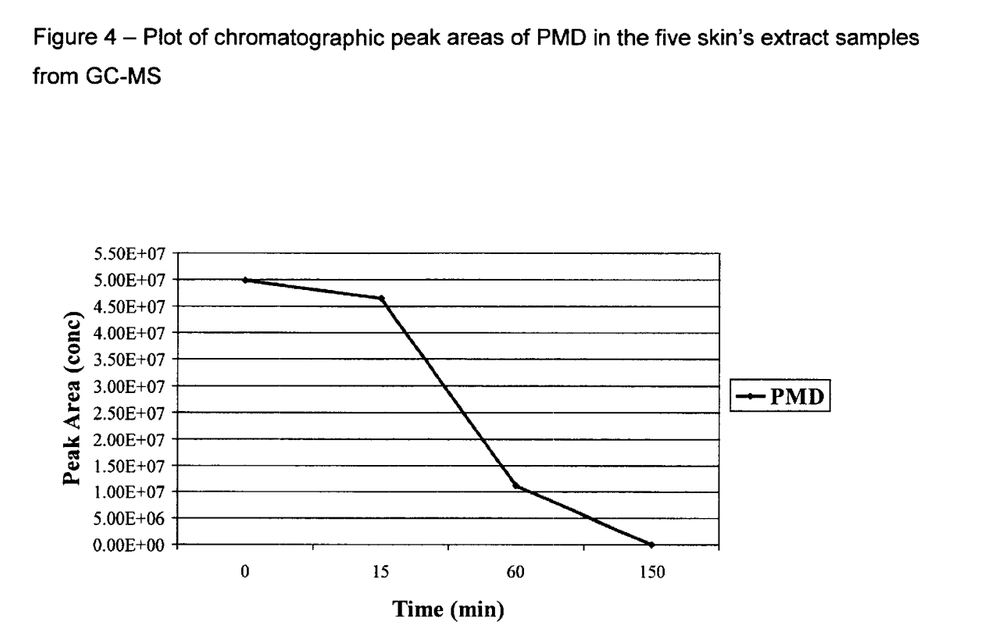
FIG. 4 is a plot of chromatographic peak area for PMD in five skin's extract samples from GC-MS.
Figure 5:
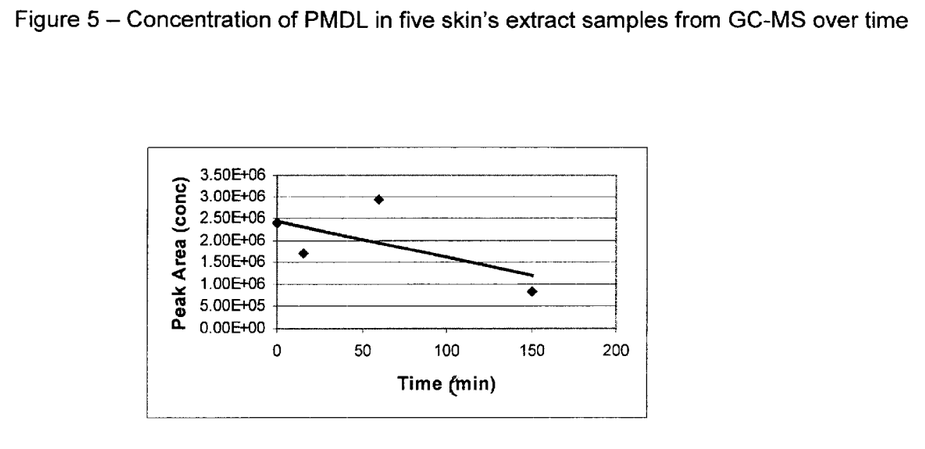
FIG. 5 is a plot of chromatographic peak areas for PMDL in 5 skins extract samples from GC-MS. Decrease in PMDL is attributable to hydrolysis of PMDL into PMD and linoleic acid.
Figure 6:
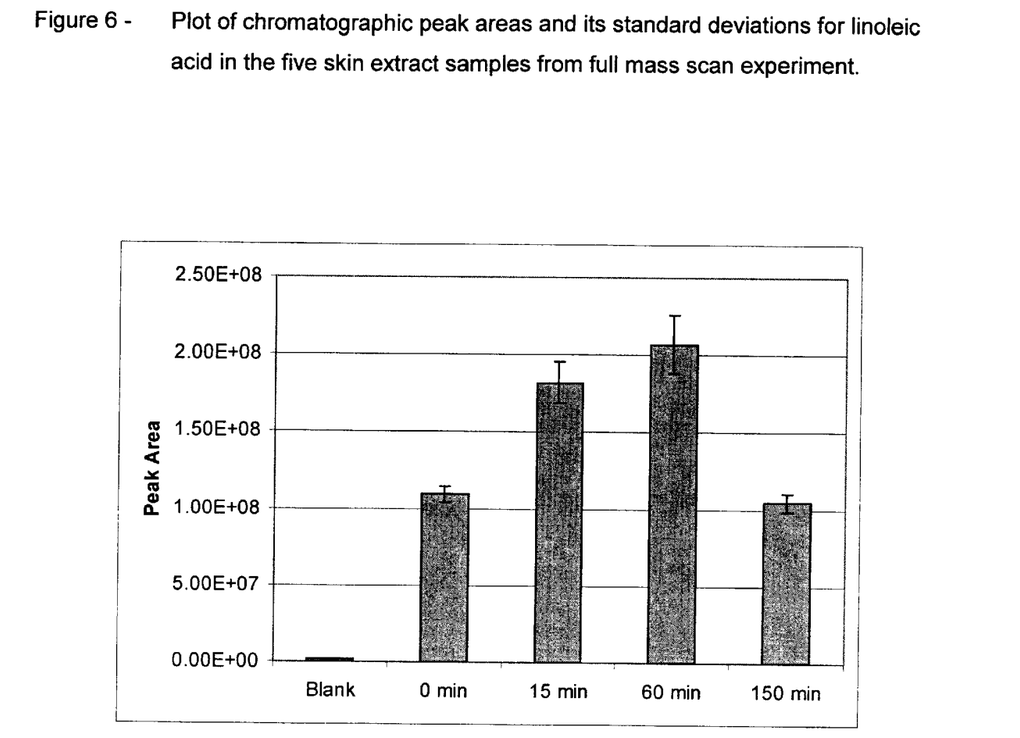
FIG. 6 is plot of chromatographic peak areas for linoleic acid in the five skin extract samples. The plot shows increase in linoleic on treated skin in first hour followed by a decrease, presumably due to adsorption into deeper layers. There is linoleic acid increase when PMDL is added.

Another set of experiments was conducted to confirm the results obtained earlier from SPME-GC for PMD & PMDL and also to confirm hydrolysis of PMDL into linoleic acid and PMD on the skin by ethanol extraction of the skin followed by GC-MS and APCI-MS analysis of the collected extracts. In this set, individual stock solutions of PMD and PMDL were prepared by placing 0.0978 g PMD and 0.1095 g in 5 mL of ethanol, respectively. Then five areas of skin, about 7 cm² on each arm, were selected. One of the five spots on each arm remained untreated as control and marked as a blank. The remaining four areas on the right arm were dosed with 32 μL PMDL and the remaining four areas on the left arm were dosed with 36 μL of PMD. Untreated area 1, and the treated area on each arm marked as 2, 3, 4, and 5, were then extracted with 4 mL of ethanol for a period of 3 min at 0, 15, 60 and 150 min intervals, respectively. Collected extracts were then analyzed by GC-MS for their PMD and PMDL and by APCI-MS for their linoleic acid contents (FIGS. 4, 5, 6 and 7). FIG. 4 is plot of PMD, FIG. 5 is plot of PMDL; and FIGS. 6 and 7 are plots for linoleic acid.

Atmospheric Pressure Chemical Ionization with Mass Spectrometric Detection (APCI-MS)

APCI-MS was used to analyze linoleic acid in ethanol skin extracts. All the experiments were performed on a Quattro Ultima (Micromass, UK) triple quadrupole mass spectrometer operated with MassLynx v3.5 software. Samples were introduced via a 50 μL loop injection valve. Reagent-grade ethanol was used as the carrier solvent and maintained at a flow rate of 200 μL/min by an Agilent HPLC 1100 system. Both full mass scan and selected ion recording (SIR) in negative ion mode were used to analyze linoleic acid which has a molecular ion (M–H)⁻ of 279.3 amu. The APCI source conditions were as follows: Corona discharge current, 18 μA, cone voltage, 70V, source temperature, 110° C., desolvation temperature, 400° C., cone gas flow, 156 L/Hr, desolvation gas flow, 315 L/Hr, photo multiplier, 600 V and full mass scan range, 100 to 700 amu. Samples from the last set of experiments, as described in the SPME experiment section were analyzed for their linoleic acid level using this technique. Each extracted sample was analyzed in triplicate.

Discussion

Analysis of a PMD standard solution of 100 μg/mL in ethanol by GC-MS showed that the PMD peak has a major mass/charge (m/z) 59, 81 (100%), 96, 139 appearing at 14.37 min. Analysis of PMDL standard solution of 100 μg/mL showed that PMDL has a peak with major mass/charge (m/z) 81(100%), 95, 137, 208, 279, 341 appearing at 38.01 min. These information were then used for identification of PMD and PMDL from other matrixes by GC-MS. Compounds indicated as PMD or PMDL in GC-MS should have a close retention, fragmented ions with m/z as shown and a similar abundance distribution pattern under the same GC program as indicated for the respective molecule.

Figure 3B:
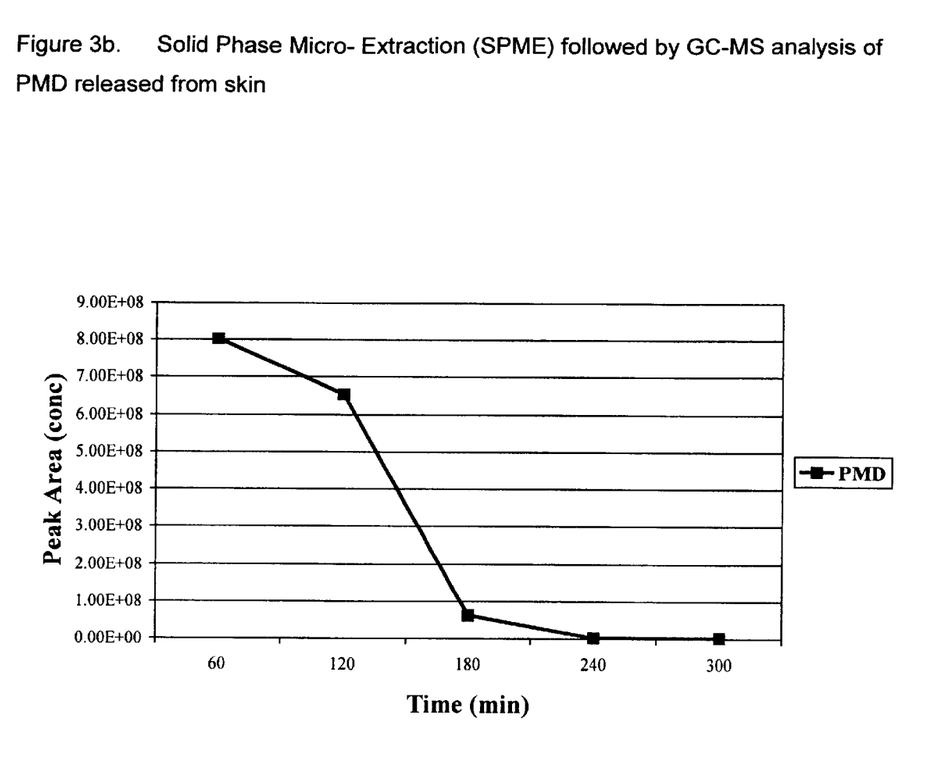

SPME was coupled with GC-MS employed to determine the evaporation profiles of PMD from the skin (FIG. 2). To confirm that SPME sample preparation technique can be used to collect the PMD vapour for further analysis by GC-MS, PMD crystals was placed in a vial with an airtight cap over night to reach equilibrium between vapour and solid phases. A SPME fiber was inserted into the vial and then removed after a known period of time was and analyzed by GC-MS. The presence of PMD was confirmed by a peak at about 14.49 min with fragmented ions with m/z 59, 81, 96, and 139. In the first SPME experiments, 174.4 μg/cm² PMD was placed on the forearm skin and its vapour was collected for 30 min. The high concentration of collected PMD vapour in the SPME fiber flooded the GC-MS column. Consequently for the second set, the levels of PMD placed on the skin and the sampling time was reduced from 174.4 μg/cm² and 30 min to 40 μg/cm² and 5 min, respectively. In this case, the PMD signal was diminished and could not be detected after 2 hours. To increase the sensitivity of detection by GC-MS, the extraction time by SPME fiber was increased again from 5 to 30 min. PMD levels placed on the skin, however, remained the same at 40 μg/cm². The PMD signal was followed and detected up to 5 hours, (FIG. 3b). The SPME/GC-MS results showed that the levels of PMD on the skin decreased as the leave on time proceeded from 0 to 300 minutes (5 hours). The findings of FIG. 3b thus confirm evaporation and slow release of PMD from the skin into the surrounding environments over a period of time to impart long-term insect repellency benefits onto the skin.

The SPME/GC-MS results also showed that PMDL itself could not be detected by this sampling technique. Therefore, PMDL profile was determined indirectly by monitoring generated PMD from hydrolysis and break down of PMDL on the skin. The obtained results confirmed hydrolysis of the PMDL into the PMD, by presence of high levels of PMD released from the skin at the early stage and then through a decrease in the PMD levels over period of time due to consumption of PMDL on the skin (See FIG. 3a). It has to be noted that SPME/GC-MS analysis of the pure PMDL earlier confirmed absence of PMD in the PMDL oil used in these experiments. This means that the PMD detected in these experiments indeed was generated from hydrolysis of PMDL on the skin.

To confirm the PMD the vaporization profile and the PMDL hydrolysis profile and to demonstrate PMDL break down into linoleic acid and PMD, a new set of experiments were designed. These experiments involved extraction of the PMD- and PMDL-treated sites with ethanol followed by GC-MS and APCI-MS analysis of the collected extracts. The obtained results from this set confirmed earlier findings for both PMD and PMDL by SPME/GC-MS analysis. Extraction coupled by GC-MS analysis showed that the PMD levels on the PMD treated skin decreased as the leave on time increased from 0 to 150 minutes. This decrease is attributed to evaporation of the PMD from the skin's surface into the surrounding environments (FIG. 4). GC-MS analysis of PMDL treated skin ethanol extracts showed a trend of decrease in the levels of PMDL on the skin as the leave on time increased from 0 min to 150 min. (FIG. 5). This decrease can be attributed to the hydrolysis of the PMDL into PMD and linoleic acid on the skin as shown earlier by SPME/GC-MS analysis, (FIG. 3a). The exceptional increase at 60 minutes showed in FIG. 5 may possibly be attributed to excess application of PMDL on the skin in the time of the experiment.

Extraction coupled with APCI-MS was used to confirm formation of linoleic acid from hydrolysis of PMDL on the skin. In APCI-MS analysis, both full mass scan and selected ion recording in negative ion mode were used. In the full mass scan experiment, the peak area in the extracted ion [$(M-H)^-$, 279.3 amu] chromatogram was utilized for quantitation while in the SIR experiment peak area was directly utilized. The full mass scan spectra of ethanol extracted untreated (blank) and PMDL treated skin were measured. The untreated skin contained relatively lower levels of linoleic acid compared to the other components present in the skin matrix. The average peak area and its standard deviation from triplicate plotted as a function of extraction time are shown in FIGS. 6 and 7 (6 corresponds to SIR data and 7 to full scan data). In both figures the level of linoleic acid is substantially higher in the treated skin samples compared to the untreated skin (blank) sample. Both plots also exhibit similar trends for linoleic acid levels over time except that the result at time zero in FIG. 6 is the highest compared to all the other times. This inconsistency remains to be investigated but may be related to sample degradation as the SIR and full scan experiments were run on separate consecutive days. Examination of the remainder of each plot reveals an increase in linoleic acid level over the 15 to 60 min period followed by a decrease at 150 min This drop in signal at 150 min is presumably due to adsorption or decomposition of linoleic acid in skin. The trends observed in FIGS. 6 and 7 confirm that linoleic acid levels increase when PMDL is applied to skin.

In summary, the obtained results confirmed that PMDL indeed hydrolyses and breaks down into PMD and linoleic acid molecules upon its delivery onto the skin. Upon their formation, the PMD would then vaporize and release into the surrounding environments and the linoleic acid absorbs into the skin.

What is claimed is:

1. A personal wash and/or personal care composition comprising an insect repellent comprising $C_{12}$–$C_{24}$ saturated or unsaturated ester of para-menthane 3,8-diol.

2. A method for providing insect repellency for period greater than 1 hours which method comprises applying to skin a composition comprising $C_{12}$–$C_{24}$ saturated or unsaturated ester of para-methane-3,8-diol.

* * * * *